United States Patent [19]

Mazal

[11] 4,350,477
[45] Sep. 21, 1982

[54] PNEUMATIC PULSATILE FLUID PUMP

[76] Inventor: Charles N. Mazal, Sullivan 119, Mexico 4, D.F., Mexico

[21] Appl. No.: 789,353

[22] Filed: Apr. 20, 1977

[51] Int. Cl.³ .............................................. F04B 45/06
[52] U.S. Cl. .................................... 417/384; 417/385; 417/389; 417/478; 91/50
[58] Field of Search ............... 417/394, 395, 385, 478, 417/389, 383, 384; 92/90, 103 M, 13.2; 91/50, 394, 325; 60/584

[56] References Cited

U.S. PATENT DOCUMENTS

| | | | |
|---|---|---|---|
| 6,668 | 9/1875 | Millward | 92/103 M |
| 1,301,485 | 4/1919 | Mueller | 417/388 |
| 1,684,530 | 9/1928 | Bast | 92/103 M |
| 1,920,146 | 7/1933 | Hueber et al. | 91/50 |
| 2,160,295 | 5/1939 | Stewart | 417/384 |
| 2,322,181 | 6/1943 | Vincent | 92/103 M |
| 2,447,311 | 8/1948 | Burt | 91/50 |
| 2,704,548 | 3/1955 | Ralston | 92/103 M |
| 2,812,716 | 11/1957 | Gray | 417/389 |
| 3,030,892 | 4/1962 | Piccardo | 417/384 |
| 3,036,526 | 5/1962 | Hise | 417/389 |
| 3,039,272 | 6/1962 | Frick | 91/50 |
| 3,429,274 | 2/1969 | Nilsson | 91/50 |
| 3,456,444 | 7/1969 | Rishton | 417/384 |
| 3,814,547 | 6/1974 | Kitrilakis et al. | 417/478 |
| 3,860,968 | 1/1975 | Shapiro | 417/384 |
| 3,916,449 | 11/1975 | Davis | 417/389 |
| 4,015,590 | 4/1977 | Normann | 417/389 |
| 4,047,849 | 9/1977 | Clay | 417/384 |

Primary Examiner—Leonard E. Smith
Attorney, Agent, or Firm—W. Scott Carson

[57] ABSTRACT

A portable pumping system for administering fluids intravenously to a patient. The system has a tube connected between the fluid source and the patient with one-way valves at each end of the tube to limit the flow to one direction. A middle portion of the tube is positioned within a first chamber that is connected by a hose to a second chamber. The second chamber has a flexible member that is reciprocally moved by an arrangement that includes a housing and a source of compressed gas. The housing has a valved inlet and outlet and the flexible member forms a portion of the boundary of the housing. The valve for the outlet of the housing is attached to the flexible member which is a metallic disc inherently biased in a concave shape in relation to the housing. In operation, the flexible member inverts to a convex shape as pressure increases within the housing emitting a click. At a predetermined point, the valve attached to the flexible member vents the housing and the flexible member reverts to its concave shape emitting another click. Means are also provided to flush out the air within the enclosing means defined by the first and second chambers and connecting hose as are means for selectively increasing or decreasing the pressure within the enclosing means.

3 Claims, 8 Drawing Figures

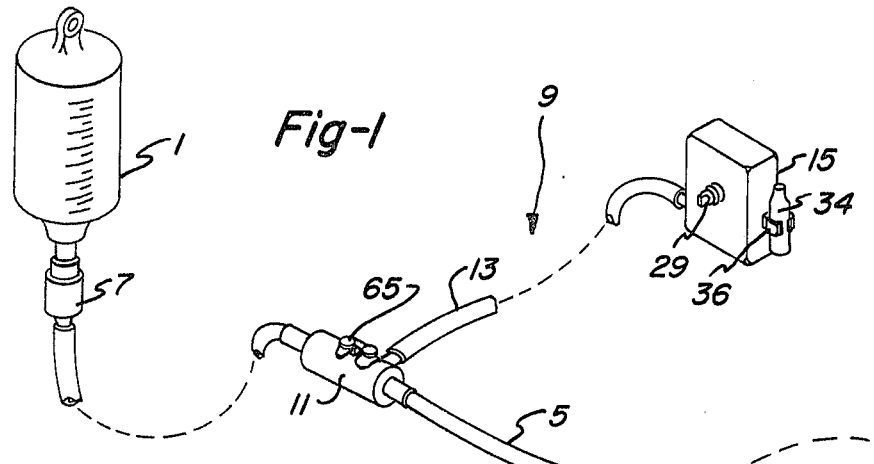
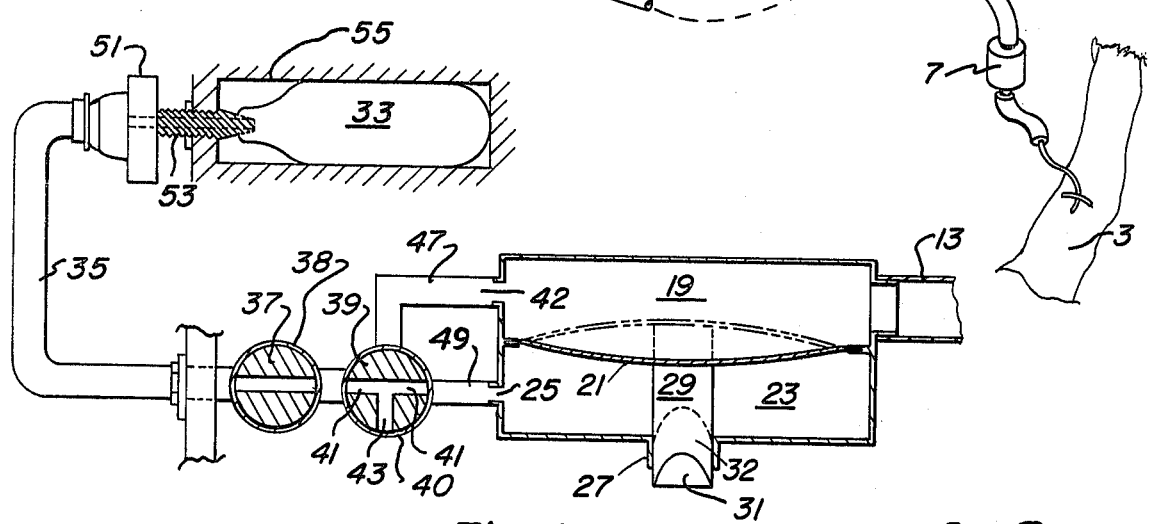
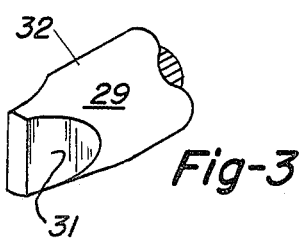
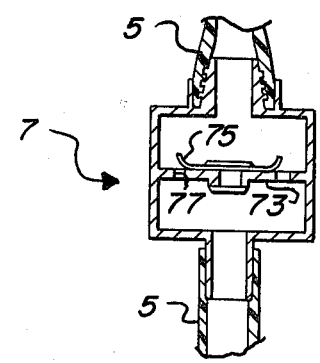
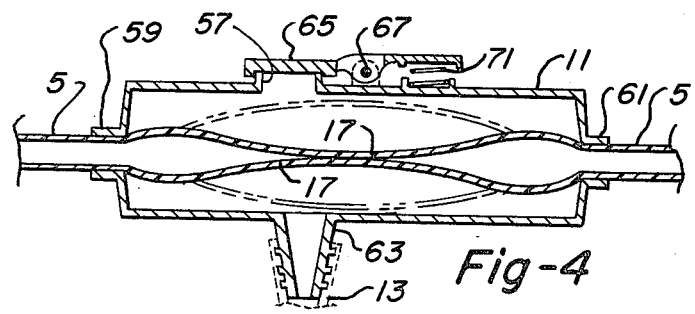

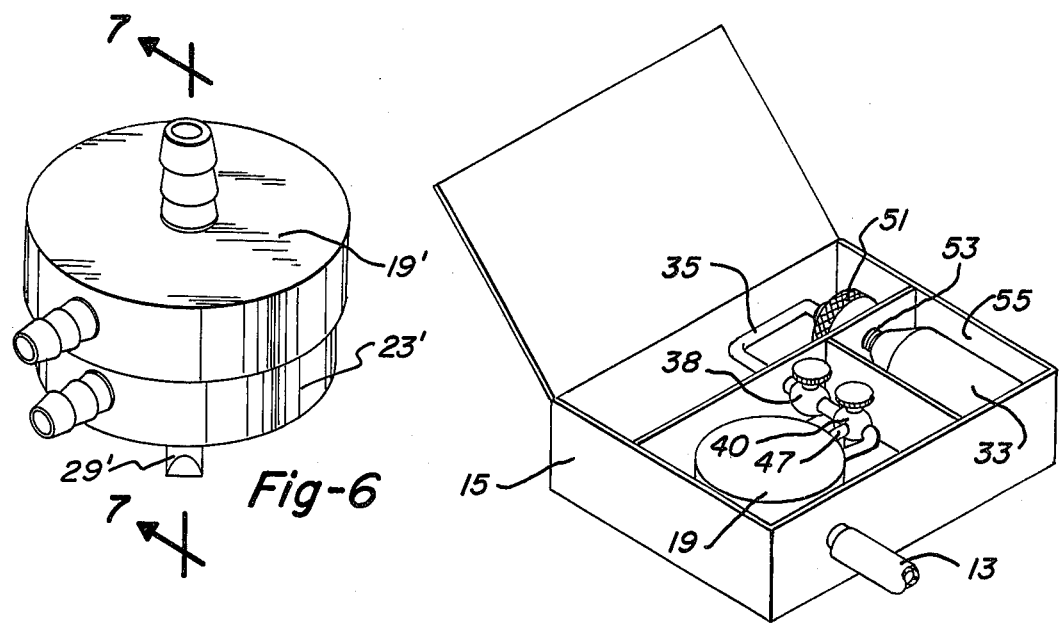
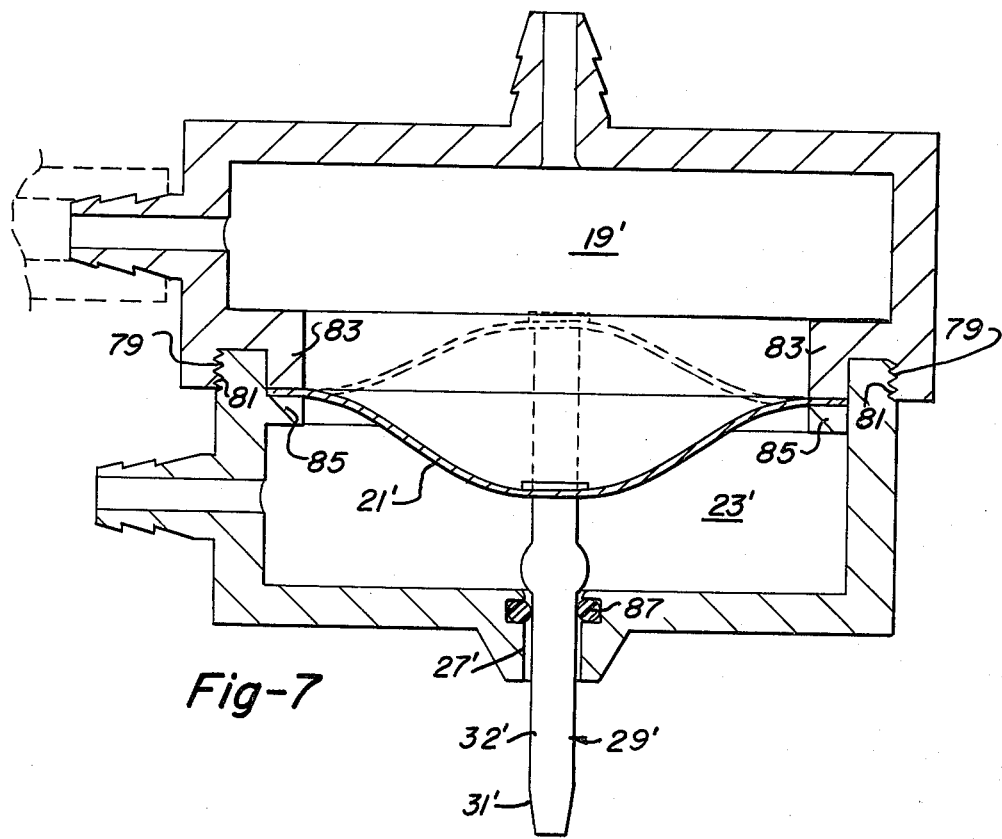

PNEUMATIC PULSATILE FLUID PUMP

FIELD OF THE INVENTION

This invention relates to the field of portable pumps for pumping fluid through a tube. The invention is particularly suited for pumping fluids intravenously into a person.

BACKGROUND OF THE INVENTION

Past methods and apparatuses for administering fluids to a stationary or ambulatory patient have primarily involved holding the source of the fluid above the patient and relying on the gravitational forces to deliver the fluids into the patient. Other methods and apparatuses rely on the venturi action of the patient's own vascular system to deliver the fluids into him. Still others use electric pumps powered by stationary or portable storage cells that can be wet or dry batteries.

Many of these systems are impractical or unreliable in emergency situations, especially battlefield emergencies. For example, it is often difficult or impossible to maintain a fluid source above a patient for gravitational feed when the patient is being rushed on a stretcher to a hospital. If the patient is being carried from a battlefield, the situation is even worse since the attendants have to concentrate more on safe movement of the patient than on keeping the fluid source held above him. Further, if it is absolutely necessary that the fluid source be held above the patient, an extra attendant is required. This additional attendant can be a very costly item on the battlefield and will greatly reduce the overall efficiency of the military and medical teams.

Systems using the venturi action of the patient's own vascular system often find the pulse of the patient too weak or irregular to be effective. These systems require constant visual monitoring by a medical attendant to make sure the patient is receiving the fluids properly. As with the gravitational systems, this exta attendant can be a most unfortunate waste of precious medical personnel.

The methods and apparatuses using electrical pumps have also proven to be unsatisfactory. Electrical pumps have numerous moving parts that can fail in addition to the paramount problems of battery upkeep and failure. These systems must be constantly checked while in storage and in use. Battery failure is usually unpredictable as well as being sudden and complete. Electrical systems are almost impossible to maintain in battlefield conditions, especially in bad weather and, furthermore, they are often bulky, costly and difficult to handle.

The ideal portable pump for intravenously feeding fluids to a patient would be simple, reliable, safe, sterile, inexpensive to make, and able to administer fluids with the source vessel above or below the patient. It would also have an adjustable pumping rate and stroke as well as interchangeable, disposable, and reuseable parts. Further, it would need a minimum of personnel and effort to operate, would not require constant visual monitoring, and would be easily and quickly convertible to a gravity feed system should the pumping mechanism fail. The present invention provides such a pump.

SUMMARY OF THE INVENTION

This invention involves a simple and reliable pump design. The pump is particularly suited for pumping fluids intravenously into a patient. The invention is powered by a source of compressed gas and has only one moving part that not only drives the pump but also emits a distinct clicking sound to alert the operator that the pump is working. This clicking feature is especially important when the pump is being used to administer life sustaning fluids into a patient because it frees the attendants from having to visually monitor the operation.

The invention is designed to be used with a tube having a flexible middle portion and end portions extending outwardly therefrom. Each end portion of the tube has a one-way valve to limit the flow of fluid therethrough to one direction. One end of the tube is connected to the source of the fluid to be administered intravenously and the other end has a needle to be inserted into the patient. The invention includes a means surrounding said flexible middle portion to enclose a volume of gas and define a closed system. The end portions of the tube extend outwardly of the enclosing means. The enclosing means has a flexible boundary member that is reciprocally moved to create cyclic pressure pulses in the enclosed volume of gas about the middle portion of the tube. The flexible middle portion of the tube is cyclically compressed by the pressure pulses to pump fluid out of the tube through one end thereof. During a trough of a pressure pulse, the flexible portion of the tube expands and draws fluid into the tube through the other end thereof connected to the source of fluid to be administered.

The flexible boundary member of the enclosing means is a metallic disk biased in a curved shape extending in a direction outwardly of the enclosing means. The flexible member forms a common boundary with a housing which has a gas inlet and a gas outlet. A valve member is attached to the flexible member and alternately opens and closes the gas outlet of the housing in response to movement of the flexible member. In its biased shape, the flexible member is convex in reference to the enclosing means and concave in reference to the housing. Compressed gas such as carbon dioxide ($CO_2$) is fed into the housing through the inlet to increase the pressure therein and move the flexible member in a direction outwardly of the housing. As the flexible member is moved outwardly, it inverts from its concave shape in reference to the housing to a convex shape and emits a distinctive click. The valve member attached to the flexible member moves with it and opens the gas outlet of the housing when the flexible member reaches a predetermined, convex position extending in a direction outwardly of the housing. The gas under pressure within the housing is vented out the gas outlet when the flexible member reaches the predetermined conves position and the flexible member snaps back to its biased concave shape emitting a clicking sound and moving the valve member to close the gas outlet. A new cycle is then begun as the compressed gas entering the housing inlet increases the pressure therein and again moves the flexible member in a direction outwardly of the housing. The frequency of the reciprocal motion of the flexible member can be adjusted by varying the rate of flow of compressed gas into the housing. This is accomplished by providing an adjustible valve between the source of the compressed gas and the housing inlet.

The enclosing means further includes a valved inlet and a valved outlet. The compressed gas used to move the flexible member is selectively connected to the valved inlet of the enclosing means. The air in the enclosing means can be flushed out by opening the inlet and outlet valves. This feature is especially important when the pump is used with a tube intravenously feeding fluid to a patient. By using a biocompatible gas such as carbon dioxide ($CO_2$) as the compressed gas, the air originally within the enclosing means about the middle portion of the tube can be flushed out and replaced by carbon dioxide ($CO_2$). If the tube should rupture and some gas pass into the patient, it would be readily absorbed without the danger of embolism. The inlet and outlet valves of the enclosing means can be selectively operated to increase or decrease the pressure within the enclosing means. By opening the inlet valve and closing the outlet valve, the pressure can be increased and by closing the inlet valve and opening the outlet valve, the pressure can be decreased. The relative pressure within the enclosing means will affect the size of the stroke of the pump and consequently, the quantity of intravenous fluid delivered with each stroke.

The source of compressed gas is a cartridge of carbon dioxide ($CO_2$) that can be easily replaced as it becomes exhausted. The attendant can tell by slowing or cessation of the clicking of the flexible member when the cartridge needs to be replaced. As an additional safety feature, the housing, enclosing means, and tube have transparent walls for quick visual inspection of the pumping mechanism and the fluid being pumped through the tube.

In one embodiment, the enclosing means includes two chambers removably connectable in fluid communication. The flexible portion of the tube carrying the intravenous fluid is mounted within the second chamber as a unit. The tube and second chamber unit can be easily removed and replaced by a new unit as needed. The disposable and replaceable aspects of the invention are particularly advantageous in field emergencies because the pumping mechanism can be connected to a new tube and second chamber unit and the entire system sterilized and ready for operation in a few seconds.

A major safety feature of this invention is that it can be easily and quickly converted to a gravity feed system should the pumping mechanism fail or the compressed gas source become exhausted. This can be done by merely raising the source vessel above the patient.

OBJECTS OF THE INVENTION

It is an object of this invention to provide a new and novel pumping system that is particularly suited for administering fluids intravenously into a patient.

It is another object of this invention to provide a new and novel pump that is simple in design, reliable, and portable.

It is an object of this invention to provide a new and novel pump that has only one moving part that emits a clicking sound when it is operating to alert attendants that it is functioning properly. This clicking feature frees attendants from having to visually monitor the system.

Another object of the invention is to provide a new and novel pump system for administering fluids into a patient in a safe manner using compressed biocompatible gas such as carbon dioxide ($CO_2$). Should the tube delivering the fluid into the patient rupture, only innocuous gas from the system would enter the patient.

It is an object of this invention to provide a new and novel pump with an adjustable pumping rate.

Another object is to provide a new and novel pump with an adjustable pumping stroke.

It is also an object of this invention to provide a new and novel pump system for administering fluids into a patient without the need to hold the source of the intravenous fluid above the patient.

It is a further object to provide a new and novel pump system for administering fluids through a tube into a patient whereby different tubes can easily and quickly be connected to the pumping mechanism of the system in a safe and sterile manner.

Another object is to provide a new and novel pump with interchangeable, reuseable, and disposable parts.

It is an object to provide an new and novel pump system for intravenously feeding fluids to a patient, which system is safe, inexpensive, easy to operate, and sterile.

Another object of the invention is to provide a new and novel intravenous pumping system that can operate with the fluid source positioned above or below the patient.

Other objects and features of this invention will become apparent by reference to the following specifications and drawings.

BRIEF DESCRIPTION OF THE DRAWINGS

FIG. 1 is a perspective view of the pumping system of the invention in use to administer fluids intravenously to a patient.

FIG. 2 illustrates the portion of the pumping system contained within the case 15 of FIG. 1. This portion includes the source of compressed gas, the housing with the reciprocally moving flexible boundary member, and the first chamber of the enclosing means. The reciprocating flexible member forms a common boundary between the housing and the first chamber of the enclosing means.

FIG. 3 shows the bottom portion of the valve controlling the outlet of the housing.

FIG. 4 illustrates the second chamber of the enclosing means which surrounds the enlarged, middle portion of the tube. The first and second chambers of the enclosing means are connected by a hose. The tube and second chamber of the enclosing means are designed to be built as a unit that can be easily removed from the rest of the pumping system and replaced by a new unit.

FIG. 5 illustrates the one-way butterfly valve located at each end of the tube.

FIG. 6 shows another arrangement of the housing and first chamber of the enclosing means.

FIG. 7 is a view along line 7—7 of FIG. 6 illustrating the internal elements of this embodiment and showing the relative movement of the flexible member.

FIG. 8 is a perspective view of the inside of the case 15 showing the relative placement of the driving elements for the pumping system.

DETAILED DESCRIPTION OF THE PREFERRED EMBODIMENTS

As best seen in FIG. 1, fluid in the source vessel 1 is being pumped into the arm 3 of the patient through the tube 5. The tube 5 has one-way valves 7 at each end to restrict the flow through the tube to one direction. The pumping system 9 of the invention includes chamber 11, connecting hose 13, and the driving elements which are contained in the case 15.

Chamber 11 of the pumping system 9 surrounds the enlarged, middle portion 17 of the tube 5 as shown in FIG. 4. Chamber 11 is connected by hose 13 to another chamber 19 located within the case 15 as illustrated in FIG. 2. If desired, chamber 11 can be directly and removably attached to chamber 19 without the addition of hose 13. Chamber 19 has a flexible member 21 that forms a common boundary member with the housing 23. The flexible member 21 is a metallic disk inherently biased by forces within the flexible member 21 in a concave shape in relation to the housing 23. Housing 23 has an inlet 25 and an outlet 27. Valve 29 controls the flow through the outlet substantially cylindrical 27 and is attached to the flexible member 21. Valve 29 is a cylindrical member that has a pinched lower portion 31 truncating the valve 29 on both sides as illustrated in FIGS. 2 and 3 forming a venting means. The valve 29 also has a vent preventing portion 32 spaced upwardly from the pinched portion 31 having substantially the same cross-sectional area and shape as the fluid outlet 27 and forming a fluid-tight seal therewith.

Container 33 is a source of compressed gas and is also located within the case 15. Container 33 is connectable by line 35 through valves 37 and 39 to the chamber 19 or housing 23. Valve 37 in valve housing 38 is used to control the flow rate of compressed gas from the container 33 and valve 39 in valve housing 40 is used to selectively connect the compressed gas from container 33 to either chamber 19 or housing 23 through the respective inlets 42 and 25. Valve 39 has T-shaped channels 41 and 43. Each valve 37 and 39 can be positioned to cut off the flow to lines 47 and 49 leading to the chamber 19 and housing 23 and valve 39 can be used as an on-off valve whereby valve 37 will not have to be reset at the start of each use. The container 33 of compressed gas can be easily removed and replaced by turning knob 51 to move the hollow screw 53 away from the container 33. Reserve compressed gas container 34 which is supported by clip 36 on case 15 in FIG. 1 can then be positioned within the compartment 55 of the case 15 and knob 51 turned to move the hollow screw 53 toward the new container 34 to break the seal and place the line 35 in fluid communication with the compressed gas in container 34.

Chamber 11 as shown in FIG. 4 has four passages 57, 59, 61, and 63 leading to the interior thereof. Flow through passage 57 is controlled by valve 65 pivotally mounted at 67 to the chamber 11. Control lever 69 is biased by spring 71 to keep the valve 65 in a closed position. The passage 65 could be valved by a screw valve or needle valve. Passages 59 and 61 sealingly receive tube 5. Preferably, tube 5 and chamber 11 are made as one unit with tube 5 bonded to chamber 11 within passages 59 and 61 to form a tight seal. Tube 13 is removeably attached to the passage 63 of chamber 11 so that tube 5 and chamber 11 can be removed and replaced as a unit. Chamber 11, hose 13, and chamber 19 form an enclosing means that can be valved shut at 39 and 65 to form a closed system.

In operation, container 33 of compressed gas is positioned in the compartment 55 of the case 15 and knob 51 is turned to advance hollow screw 53 to place the line 35 in fluid communication with the compressed gas in container 33. Valves 37 and 39 are first positioned in a flushing mode to allow the compressed gas to flow into chamber 19. In this mode, valve 65 of the chamber 11 in FIGS. 1 and 4 is also opened. With valve 65 opened and valves 37 and 39 aligned to direct compressed gas into chamber 19, the air in the enclosing means (chamber 19, hose 13, and chamber 11) can be flushed out and replaced by the gas from container 33. In the preferred embodiment, the compressed gas is a biocompatible gas such as carbon dioxide ($CO_2$) so that should the middle portion 17 of the tube 5 rupture and gas pass into the patient, it would be readily absorbed without the danger of embolism. The pressure within the enclosing means (chamber 11, hose 13, and chamber 19) can be selectively set by manipulating the valves 39 and 65. By closing valve 65 and opening valve 39, the pressure can be increased and by closing valve 39 and opening valve 65, the pressure can be decreased. The pressure within the enclosing means will affect the relaxed size and shape of the middle portion 17 of the tube 5.

Once the air within the enclosing means has been flushed out and replaced with the biocompatible gas from container 33 and after the pressure within the enclosing means has been adjusted to the desired level, valve 65 is closed and valve 39 is moved to direct compressed gas into the housing 23. As the pressure within the housing 23 increases, the flexible member 21 moves from its biased, concave first position in a direction outwardly of the housing 23. Valve 29 is attached to the flexible member 21 and moves with it. As the flexible member 21 continues to move in a direction outwardly of the housing 23, it inverts and assumes a convex shape, emiting a distinctive click. When the flexible member reaches its second position, shown in dotted lines in FIG. 2, the lower pinched portion 31 of valve 29 has been raised enough to vent the gas within the housing 23 out the outlet 27. The gas vents quickly and flexible member 21 snaps back to its original concave first position, emiting a second click. Valve 29 moves with the flexible member 21 and again closes the outlet 27 of the housing 23 to begin a new cycle.

The rate of reciprocal motion of the flexible member 21 can be varied by adjusting the flow rate of the compressed gas into the housing 23 through valve 37. The difference between the relaxed position of the middle portion 17 of the tube 5 and its compressed position as shown in FIG. 4 determines the amount of fluid pumped through the tube 5 with each stroke. The size of the stroke can be varied by adjusting the ambient pressure within the enclosing means. This is done by manipulating valves 39 and 65 as explained above. The ambient pressure within the enclosing means will determine the relaxed position of the middle portion 17. The greater the difference between the relaxed position and the compressed position of middle portion 17, the greater will be the stroke and amount of fluid pumped with each pulse. The amount of fluid pumped with each pulse can also be adjusted by leaving valve 65 slightly open so some gas passes into and out of chamber 11 with each pressure pulse. With valve 65 slightly open, the full effect of the peak and trough of each pressure pulse is not applied completely to the middle portion 17 of tube 5. With this pumping system, the source vessel 1 can be placed below or above the patient. In one manner of operation, the system is used to pump fluids into the patient until such time as the source vessel 1 can be safely secured above him. The pump can then be turned off and the fluids fed by gravity through the tube 5.

FIG. 5 illustrates the elements of one-way valves 7. Each valve 7 has a perforated middle member 73 with a flexible butterfly member 75 mounted to it. Fluid can flow from bottom to top in FIG. 5 but any reverse flow will press butterfly member 75 tightly over the holes 77 of perforated member 73 to prevent flow in that direction.

The embodiment of FIGS. 6 and 7 is a modified arrangement of the chamber 19 and housing 23. Chamber 19' and housing 23' in FIGS. 6 and 7 have complementary screw grooves 79 and 81. Flexible member 21' can be positioned between flanges 83 and 85 and the chamber 19' and housing 23' screwed together to secure the flexible member 21' in place. This embodiment also has an O-ring 87 forming a part of the fluid outlet 29' to slideably and sealably receive the vent preventing portion 32' of the stem of valve 29'. As with the embodiment of FIGS. 1–4, chamber 19' could be removeably connectable directly to chamber 11 or hose 13 can be used to connect them.

While two embodiments of the present invention have been described in detail herein, various changes and modifications can be made without departing from the scope of the invention

I claim:

1. A device for creating a cyclic pressure pulse in a closed volume of fluid, said device comprising:
   means enclosing a volume of fluid for defining a closed system, said means including a flexible member forming a boundary portion of said enclosing means, said flexible member being biased in a first position extending in a direction outwardly of said enclosing means and movable to a second position extending in a direction inwardly of said enclosing means,
   drive means for moving said flexible member from said biased first position to said second position, said driving means including
   (i) a housing having a fluid inlet and a fluid outlet,
   (ii) valve means operably connected to said flexible member for alternately opening and closing said fluid outlet, said valve means opening said fluid outlet when said flexible member is in said second position, and
   (iii) a source of fluid under pressure operably connected to said fluid inlet of the housing to increase the pressure within said housing to move said flexible member inwardly of said enclosing means to said second position whereupon said valve means opens said fluid outlet of the housing to vent the pressurized fluid within said housing and allow said flexible member to return to the biased first position to begin a new cycle in which said source of fluid under pressure again increases the pressure with said housing to move said flexible member inwardly of said enclosing means,
   said enclosing means includes a fluid inlet and a fluid outlet, said inlet and outlet each having a valve means for controlling the passage of fluid therethrough, and,
   said device further includes a source of fluid under pressure connected to said fluid inlet of the enclosing means whereby each of the valve means for said inlet and outlet can be opened to flush fluid out of said enclosing means and each of said valve means can be selectively operated to raise the pressure of the fluid in said enclosing means by opening the valve means for the inlet and closing the valve means for the outlet and operated to lower the pressure of the fluid in said enclosing means by closing the valve means for the inlet and opening the valve means for the outlet.

2. The device of claim 1 further including:
   tube means having a flexible portion passing through said enclosing means and two end portions extending outwardly of said enclosing means, said flexible portion assuming a first shape and each of said end portions having a one-way valve means to limit flow through said tube means to one direction, the cyclic pressure pulses created within said enclosing means compressing said flexible portion of said tube means during a peak in one of said cyclic pressure pulses to force fluid out of said tube in said one direction means through one of said valve means, said flexible portion of the tube means expanding toward said first shape during a trough in one of said cyclic pressure pulses to draw fluid into said tube means in said one direction through the other valve means whereby fluid enters and exits said tube means in pulses.

3. The device of claim 1, further including:
   valve means for regulating the rate of fluid flowing from the fluid source under pressure into said housing to control the frequency of the motion of the flexible member between said first and second positions.

* * * * *